US009302105B2

(12) United States Patent
ÓLaighin et al.

(10) Patent No.: US 9,302,105 B2
(45) Date of Patent: Apr. 5, 2016

(54) MUSCLE STIMULATION DEVICE (71) Applicants: NATIONAL UNIVERSITY OF IRELAND, GALWAY, Galway (IE); UNIVERSITY OF LIMERICK, Limerick (IE)

(72) Inventors: Gearóid Ó Laighin, Ennis (IE); Paul Breen, Emly (IE); Derek O'Keeffe, Limerick (IE); Richard Conway, Annacotty (IE); Sinziana Lulia Birlea, Cluj-Napoca (RO)

(73) Assignees: NATIONAL UNIVERSITY OF IRELAND, GALWAY, Galway (IE); UNIVERSITY OF LIMERICK, Limerick (IE)

( * ) Notice: Subject to any disclaimer, the term of this patent is extended or adjusted under 35 U.S.C. 154(b) by 0 days.

(21) Appl. No.: 14/357,326

(22) PCT Filed: Nov. 9, 2012

(86) PCT No.: PCT/IE2012/000048
§ 371 (c)(1),
(2) Date: May 9, 2014

(87) PCT Pub. No.: WO2013/069003
PCT Pub. Date: May 16, 2013

(65) Prior Publication Data
US 2014/0343625 A1    Nov. 20, 2014

(30) Foreign Application Priority Data
Nov. 11, 2011   (IE) .................................... 2011/0492

(51) Int. Cl.
*A61N 1/36*      (2006.01)
*A61N 1/14*      (2006.01)

(52) U.S. Cl.
CPC ............... *A61N 1/36014* (2013.01); *A61N 1/14* (2013.01); *A61N 1/36003* (2013.01); *A61N 1/36125* (2013.01)

(58) Field of Classification Search
CPC . A61N 1/3787; A61N 1/37252; A61N 1/375; A61N 1/36003; A61N 1/36125; A61N 1/08; A61N 1/36014; A61N 1/3758; A61N 1/0452; A61N 1/0472; A61N 1/3606; A61N 1/378; A61N 1/3925; A61N 1/3937; A61N 1/37; A61N 1/3625; A61N 1/3912; A61N 1/3981; A61N 1/00; A61N 1/14; A61N 1/303; A61B 2560/0214; H01M 10/44; H03K 3/78
See application file for complete search history.

(56) References Cited

U.S. PATENT DOCUMENTS 4,895,153 A   1/1990   Takeuchi et al.
5,593,427 A   1/1997   Gliner et al.
(Continued)

OTHER PUBLICATIONS
International Preliminary Report on Patentability; PCT/IE2012/000048; May 13, 2014.
(Continued)

*Primary Examiner* — Deborah Malamud
(74) *Attorney, Agent, or Firm* — Studebaker & Brackett PC (57) ABSTRACT

A surface NMES stimulation device the device has a control processor, a voltage regulator connected to a high voltage supply, a bridge of control switches, and electrodes or electrode terminals connected in the bridge to receive drive signals via the control switches. The processor directs a drive scheme for the bridge control switches in which charge build-up on a user's skin is allowed to dissipate to ground in an inter-pulse interval. An isolation capacitor isolates the high voltage supply from the electrodes, and charging of the capacitor only occurs if a switch allows it. Sensors senses supply voltage and bridge current and the processor monitors there to determine further stimulation and faults.

26 Claims, 7 Drawing Sheets

(56) References Cited

U.S. PATENT DOCUMENTS 5,607,454 A 3/1997 Cameron et al.
6,035,237 A 3/2000 Schulman et al.
2003/0204225 A1 10/2003 Heathershaw et al.

OTHER PUBLICATIONS

International Search Report; PCT/IE2012/000048; Apr. 23, 2013.

MUSCLE STIMULATION DEVICE

FIELD OF THE INVENTION

The invention relates to surface neuromuscular electrical stimulation (NMES).

PRIOR ART DISCUSSION

The application of an electrical stimulus through the skin to a motor neuron causing activation of its associated muscle is known as surface Neuromuscular Electrical Stimulation (NMES). There are numerous uses for NMES where the electrodes are fitted to the skin surface; the prevention of atrophy, improving blood circulation, drop-foot correction, or stroke rehabilitation for example. Tolerance of the user to the surface NMES stimulus is critical in these and other applications. In long term applications where NMES is required over extended periods of time without supervision, device safety is also important for successful treatment.

When a NMES stimulus is applied via surface electrodes with the purpose of inducing muscular contraction, sensory neurons in the skin are also activated inadvertently. The resulting muscular contraction increases in proportion to the applied stimulus. However, the pain experienced at the electrode site is also amplified with increases in stimulus intensity. This pain is a limiting factor in the maximal stimulus that a user may tolerate and indirectly limits the maximal muscular contraction force that may be achieved. This pain can also affect the tolerance of a user to NMES and their likelihood to adhere to a surface NMES type treatment regimen in both short and long term applications.

Furthermore, as NMES intensity increases and forceful muscular contractions are induced, further muscular pain similar to cramping or a spasm may be perceived by the user. Again, this will limit the acceptability of NMES by the user and limit the potential benefit.

A typical biphasic-stimulus as used in NMES devices consists of a cathodal rectangular pulse with a duration in the order of 350 μs followed by an anodal rectangular pulse of equal duration and charge. The cathodal phase serves to stimulate excitable tissue and the anodal phase performs mainly charge balancing for electrochemical reasons including alkaline pH swings, hydrogen gas evolution and to prevent oxidizing agent formation that can occur at the electrode-tissue interface (Reilly, 1992). However, the anodic reversal of a biphasic stimulus can act to abolish an action potential developing in response to the cathodic phase. A delay of 100 μs or more between pulse phases was found to effectively prevent this event from occurring (Reilly, 1992). More recent studies have concluded that contrary to classic belief, the trailing phase of a biphasic pulse not only performs electrochemical reversal but also has an excitatory effect (Field-Fote et al., 2003). It has also been reported that the peak voltage needed to reach sensory and motor nerve thresholds was lower with biphasic than monophasic stimulation (Kantor et al., 1994).

Typically, stimulus is applied with biphasic stimuli repeated at a rate of 35 Hz starting with a low amplitude which increases to a preset maximum over a preset time (ramp-up time). Stimulus amplitude is maintained at this level for a preselected period (on-time) before being reduced to zero over a set preset period (ramp-down time). This stimulus envelope may then be repeated following a period of rest (off-time). A burst of stimulus is normally applied as follows: a ramp-up time, on-time at peak stimulus intensity and ramp-down time and is typically referred to as a stimulus envelope.

US2008/0215114 (Stuerzinger) describes a system for cardio-synchronised stimulation of skeletal or smooth muscle. It has a high voltage stage, called a boost converter, feeding directly a H-bridge of switches delivering power to the electrodes.

US2007/0097593 (Cyberonics Inc) describes an implantable NMES with variable output ramping, with emphasis on ramping rates. U.S. Pat. No. 6,826,427 (Fayram) describes a battery of a cardiac stimulation device, often referred to as a "pacemaker", aimed to inhibit voltage delay. U.S. Pat. No. 5,999,853 (Stoop et al) describes a dual chamber pacemaker. The above-noted problems which arise for surface NMES device do not arise for implanted stimulators such as these.

The invention is directed towards improving surface NMES stimulation devices to:
  reduce substantially the pain experienced at the skin electrode interface, and/or
  reduce substantially the extent of muscle cramp/spasm, and/or
  improve reliability and efficiency of the device.

REFERENCES

Baker, N, Murali-Krishnan, S, Rayman, G. A user's guide to foot screening. Part 1: Peripheral neuropathy. The Diabetic Foot 2005; 8(1): 28-37.

Breen, P P, O'Keeffe, D T, Conway, R, Lyons, G M. A system for the delivery of programmable, adaptive stimulation intensity envelopes for drop foot correction applications. Medical Engineering & Physics 2006; 28(2): 177-186.

Field-Fote, E C, Anderson, B, Robertson, V J, Spielholz, N I. Monophasic and biphasic stimulation evoke different responses. Muscle Nerve 2003; 28(2): 239-41.

Kantor, G, Alon, G, Ho, H S. The effects of selected stimulus waveforms on pulse and phase characteristics at sensory and motor thresholds. Physical Therapy 1994; 74(10): 951-62.

Lyons, G M, Breen, P. A unit to provide a capability for programmable real-time adjustment of stimulus intensity to a hand-held stimulator for drop foot correction, IEEE Engineering in Medicine and Biology Society, Cancun, Mexico, 2003; pp. 1554-1557.

Reilly, J P. Electrical Stimulation and Electropathology Cambridge: Cambridge University Press, 1992;

SUMMARY OF THE INVENTION

According to the invention, there is provided a surface NMES stimulation device the device comprising:
  a control processor,
  a voltage regulator connected to a high voltage supply,
  a bridge of control switches,
  electrodes or electrode terminals connected in the bridge to receive drive signals via the control switches,
  wherein the processor is adapted to direct a drive scheme for the bridge control switches in which charge build-up on a user's skin is allowed to dissipate to ground in an inter-pulse interval, and
  wherein the stimulation device comprises at least one isolation capacitor isolating the high voltage supply from the electrodes, the bridge comprises top switches linked with the isolation capacitor and bottom switches linked to ground, wherein charging of the capacitor only occurs if a switch between the high voltage supply and the capacitor is closed.

In one embodiment, the device comprises a voltage sensor for sensing voltage in the high voltage supply, and the processor is adapted to monitor said voltage and to determine further stimulation control accordingly. In one embodiment, the device comprises a current sensor for sensing current in the bridge, and the processor is adapted to monitor said current and to determine further stimulation control accordingly.

In one embodiment, the processor is adapted to use said current sensing to monitor changes in skin impedance and/or reactance in real time. Preferably, the current sensor comprises a feedback conductor arranged to provide feedback of a sensing signal from a resistance connected to the bottom bridge control switches. In one embodiment, the current sensor further comprises a current-limiting resistor connected to the bottom bridge control switches and a Zener diode in series with the resistor to protect the feedback conductor (106) from over-current and over-voltage.

In one embodiment, the processor is adapted to use a combination of said current sensing in the bridge and said voltage sensing in the high voltage supply to ensure that only a voltage required across the electrodes is applied and that the stimulation ceases if any fault is detected.

In one embodiment, the control switches comprise at least four switches in a H-bridge arrangement in which the electrodes or electrode terminals are connected across the middle of the bridge, power is delivered to the top switches from the capacitor and the bottom switches are connected to ground, wherein closing a top and a bottom switch of the bridge allows the stored charge to flow through the electrodes to ground, generating a positive pulse, and closing the other two switches allows the charge to flow in the opposite direction and generates a relative negative pulse.

In one embodiment, the processor is adapted to provide a drive scheme including:
  applying a current pulse causing a build-up of charge concentrated at the skin-electrode interface,
  applying a second pulse of opposite polarity, and
  in the interval between said pulses causing the skin-electrode charge to dissipate to ground by closing the bottom bridge switches, thereby reducing the peak current of the second pulse.

In one embodiment, the processor is adapted to close the bottom bridge control switches to allow charge built-up within the user's body, and/or concentrated at the skin-electrode interface to flow through the electrodes to ground.

In one embodiment, the processor is adapted to vary ramp times for voltage increases and decreases of the high voltage supply according to conditions while maintaining a constant ramp slope.

In one embodiment, the ramp-up and/or ramp-down time of the stimulus envelope increases with increased stimulus intensity. In one embodiment, the on-time is reduced while the ramp-up time and ramp-down time are elongated as the stimulus intensity is increased, to maintain the ramp-up rate and total envelope duration.

In one embodiment, the processor is adapted to change ramp rates in response to changes in the peak stimulus intensity. In one embodiment, the processor is adapted to make said changes by reference to a look-up table for parameters or by setting the ramp-up/ramp-down rates and adjusting the on-time parameter accordingly, or by setting starting conditions for each variable and a ratio determining how each parameter should be adjusted based on changes in the peak stimulus intensity.

In one embodiment, the isolation capacitor value is no higher than 10 μF, thereby limiting the DC-DC output voltage and current delivered to the bridge. In one embodiment, the maximum output current in the event of multiple failures (a short between the user and the DC-DC output) is 5 mA. In one embodiment, the total resistance due to the bridge control switches which are ON at any time for delivery of power to the electrodes is less than 10 Ohms.

In one embodiment, the device comprises a switch arranged to dump charge from the isolation capacitor to ground bypassing the bridge in the event of a failure detected by the processor.

In one embodiment, the device comprises a plurality of stimulation channels. Preferably, the device comprises at least six switches, in which each successive pair of top and bottom switches forms a bridge with the preceding pair of top and bottom switches. In one embodiment, the device comprises only one high voltage supply and one isolation capacitor feeding the control switches forming the bridges.

In one embodiment, the processor is adapted to apply a test charge to the isolation capacitor and to then perform a full diagnostic procedure with both maximum current and voltage applied.

In one embodiment, said testing includes incrementally increasing voltage across the isolation capacitor up to a maximum voltage and utilising the internal resistance of the device to test integrity for maximum current, and then testing electrode impedance and reactance by passing a voltage pulse across the electrodes.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 5 is a plot showing a comparison of a method of the invention for applying stimulus with a reference prior art approach;

DESCRIPTION OF THE EMBODIMENTS

Figure 1:
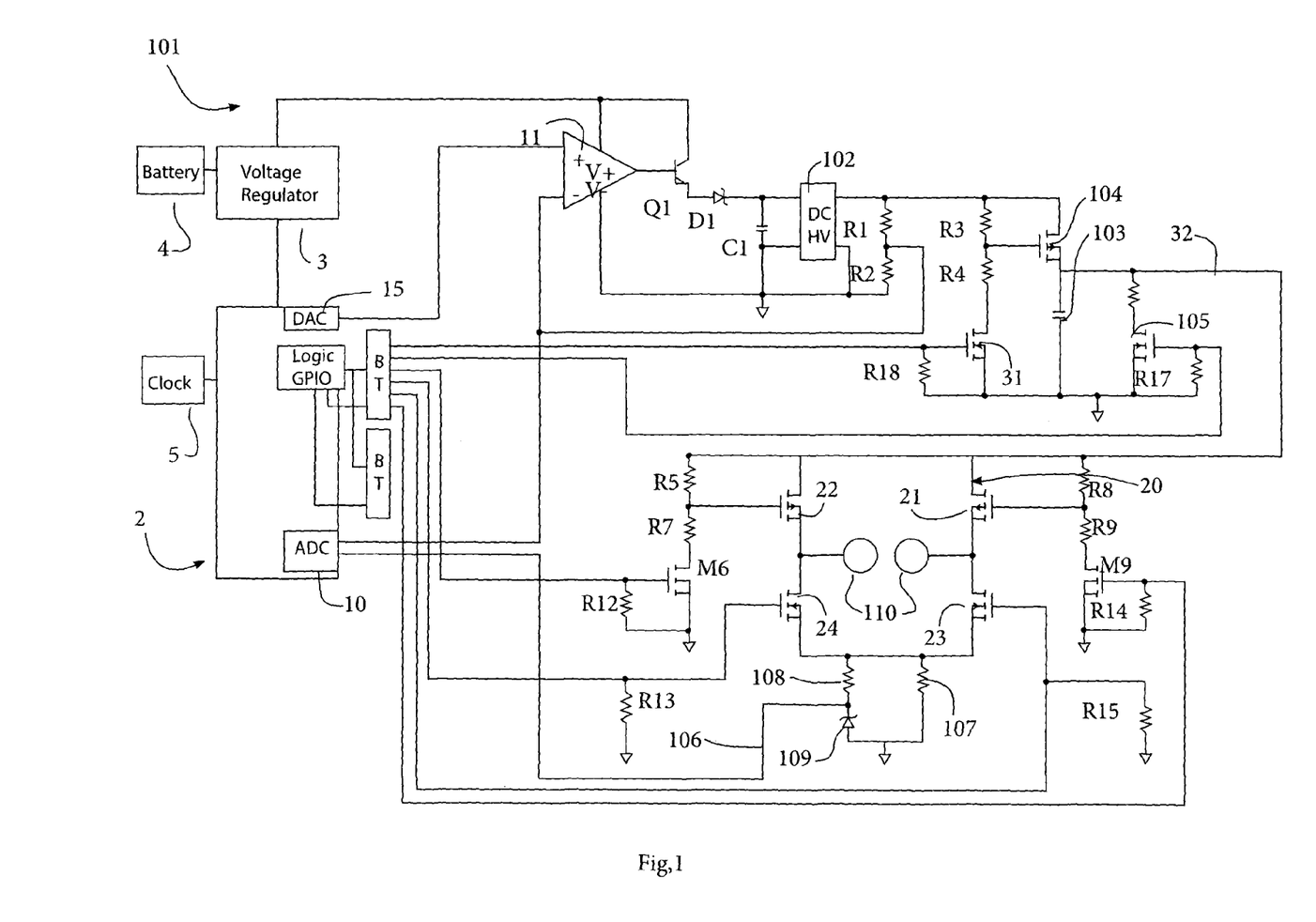
FIG. 1 is a circuit diagram of a stimulator device of the invention.
Figure 2:
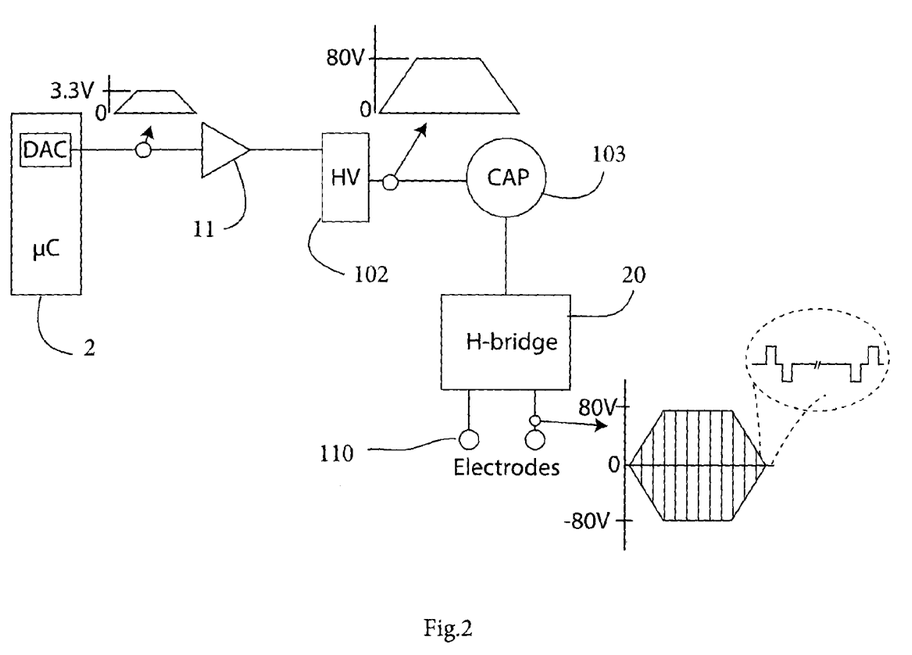
FIG. 2 shows the power flows in the circuit.

Referring to FIGS. 1 and 2 a stimulation device 101 comprises a micro-controller 2 connected to a voltage regulator 3, in turn connected to a battery DC power source. The micro-controller 2 is linked with a clock 5, and comprises an ADC 10 for sense inputs. It has a DAC 15 for providing analog control input to an op-amp 11. The op-amp 11 controls the flow of power to a high voltage supply 102. Thus, the output of the high voltage supply is an amplified DAC signal. The output of the high voltage supply 102 is connected across a pair of resistors R1 and R2, and a voltage-sensing tap from between these two resistors is linked back to the micro-controller 10 by a track 30, thereby providing a voltage feedback to the micro-controller in real time. Flow of current from the high voltage supply 102 is controlled by a FET switch 104.

The high voltage supply 102 has a 0 to 5V input voltage, n 0 to 100V output voltage, a 5 mA output current, and a typical frequency of 100 to 200 kHz.

At the lower end of the diagram of FIG. 1 a H-bridge 20 is formed by two pairs of top and bottom switches 22/24 and 21/23. Each pair has a top switch (22, 21) connected to the isolation capacitor 103 to receive power, and each pair has a bottom switch (24, 23) connected to ground via current-sensing components. A pair of electrodes 110 is connected across the two pairs. In other embodiments the device does not include the electrodes, only terminals for connection to electrodes in use.

The high voltage supply 102 is isolated from the H-bridge 20 by an isolation capacitor 103. The isolation capacitor 103 is charged via the switch 104, in turn controlled by a switch 31 the gate of which is linked with the micro-controller 2. The capacitor 103 is linked with the H-bridge 20 by a track 32. There is a by-pass switch 105 arranged to dump the charge to ground, under micro-controller 2 control if required. The voltage level of the isolation capacitor 103 is an instantaneous sample of the amplified DAC 15 level. Thus, as shown most clearly in FIG. 2, the DAC 15 generates a waveform envelope which is divided into discrete, balanced, pulse train by a combination of the isolation capacitor 103 and the H-bridge 20.

The voltage converter 102 in conjunction with the feedback arrangements provides a linear voltage output in response to a control input. Many existing stimulators create a constant high voltage and utilise a potentiometer arrangement to reduce this to the required voltage level. This results in power loss through the potentiometer. A benefit of the present invention is that only the voltage required across the electrodes is generated across the storing capacitor (103) and this reduces power loss.

The by-pass switch 105 is employed to dump charge to ground internally in the event of a failure. This may be accomplished without control of the H-Bridge components such that any detected failure does not require that the stimulation H-Bridge is used. This ensures that if an error occurs in the H-Bridge it may be made redundant by a separate mechanism. In the event that the output stimulus amplitude is to be reduced dramatically it is possible to dump charge using the same mechanism. As the resistance of the dump path is known, this may be accomplished by allowing the dump switch to close for a specific period of time. Any inaccuracy in the charge dumped will be accommodated for by the feedback mechanism R1/R2/30. It should be noted that the charge dump path is isolated from the HV supply 102 by the MOSFET 104 when in operation, the benefit of which is that as charge dump occurs, power is not being drawn from the HV supply.

Changes in skin impedance/reactance can be monitored in real time and acted upon such that damage is not caused to the users' body. Therefore, advantageously, the same mechanism is used for H-bridge testing and for skin impedance monitoring. This monitoring is accomplished through feedback on a sensing track 106 from a low value resistance 107 (10 Ohms approx.) to the microcontroller 2 which constantly monitors the current flow. This feedback is protected from over-current and over-voltage through the use of a current-limiting resistor 108 and an appropriate Zener diode 109 in series. The stimulator device 101 does not require many parts for monitoring output current and detecting operational faults, and it is not dependant on logic gates to operate. The advantage of using MOSFETs as described are that their switching times are approximately 10 times faster than all's, use very little switching current, and are less affected by temperature.

The H-Bridge 20 consists of four switches 21-24 with electrodes 110 in the middle of the switches. Power is delivered to the top two switches 21 and 22 from the supply components including the capacitor 103, and identified generally by the numeral 25. The supply current flows through the bottom two switches 23 and 24 to ground 26. Closing the switches 22 and 23 allows the stored charge to flow through the electrodes 110 to ground, generating a positive pulse. Closing the switches 21 and 24 allows the charge to flow in the opposite direction and generates a relative negative pulse.

Figure 3:
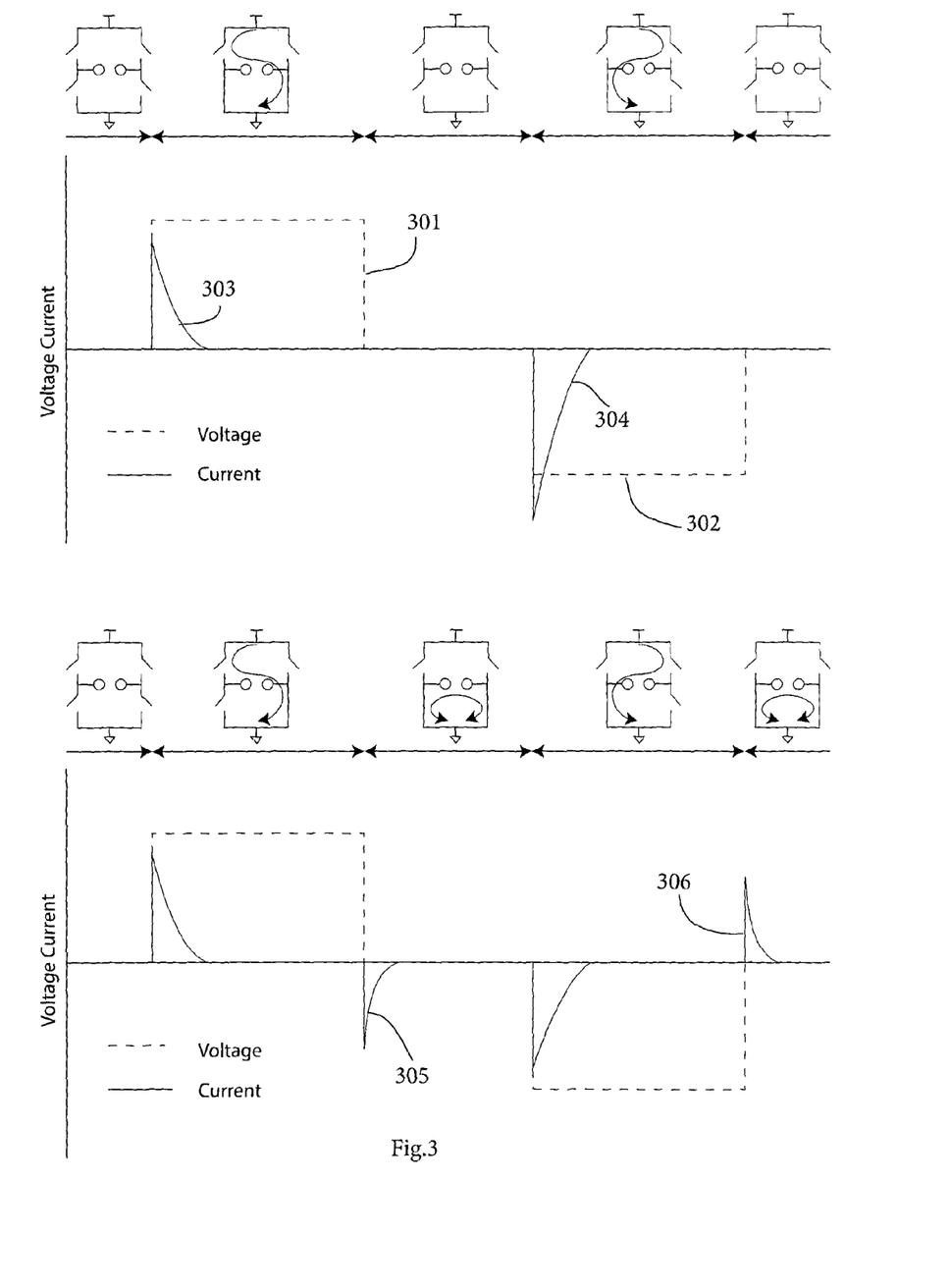
FIG. 3 is a set of plots showing the effect of allowing current dissipation.

Human skin has a capacitance associated with it and can therefore store a charge. In relation to the biphasic pulses shown in FIG. 3 the following may be ascertained. An initial voltage pulse 301 causes a current pulse 303 having typical RC characteristics. This is accompanied by a build-up of charge within the user's body, concentrated at the skin electrode interface. When the second pulse, 302, is applied we see that the current 304 applied is much larger than the first, and on first inspection there would appear to be an imbalance. However, this is due to the charge build-up due to the first pulse. Typically, this will dissipate before the next biphasic set of pulses. However, it is notable that the current flowing through the skin is almost doubled and could cause increased discomfort to the user. The micro-controller 2 is programmed to, if desired at set-up, allow this charge to dissipate to ground in the inter-pulse interval and immediately after the second pulse the peak current may be reduced. This is shown by the current spikes 305 and 306.

Furthermore, it is known that motor nerves have a shorter chronaxie period than afferent sensory nerves. "Chronaxie" is the minimum time over which an electric current double the strength of the rheobase needs to be applied, in order to stimulate a muscle fiber or nerve cell. "Rheobase" is the minimal electrical amplitude of infinite duration that results in an action potential or the contraction of a muscle. It is likely that the discharge pulse effects a reversal of the stimulation within the sensory nerve. Thus the motor nerve may be successfully activated (action potential generated) while eliminating (to some degree) action potential generation in the sensory nerve. It is for this reason that a discharge of skin capacitance is required after both positive-going and negative-going stimulus pulses.

Figure 4:
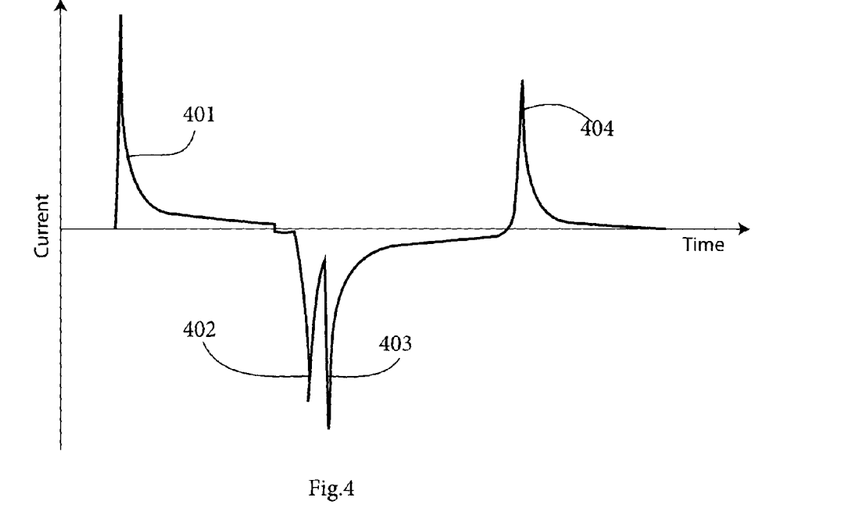
FIG. 4 shows actual measurements of current response when a stimulus is applied to the triceps surae.

The current response to this biphasic voltage pulse with the charge dissipating steps incorporated is shown in FIG. 4, as applied to a healthy adult. It may be seen that the current response to the first voltage pulse (401) has a discharge response associated with it (402). Similarly, the current response to the second voltage pulse (403) has a discharge response associated with it (404). It may be seen that due to these discharge pulses, 401 and 403 now have similar amplitudes.

Overall, the benefit of this stimulation method is that pain felt at the electrode site is effectively eliminated.

For further practical demonstration, electrodes were applied to the triceps surae of a participant lying in the supine position. Stimulus was first applied in the normal manner without discharge phases. Voltage was increased and force generated up to the maximum tolerable level for the subject. This was then repeated with the discharge phases enabled. The results are shown in FIG. 5. There are important advantages to note, including the following.

The range of force generated was greater with the discharge phases enabled.

The maximum force generated was over 160% greater with discharge phases enabled.

The only limitation to the level of stimulus applied was cramp induced in the muscle when the discharge phases were enabled. Pain at the electrode site is the limiting factor without the discharge phases.

With discharge phases enabled, a strong correlation was found between—

Voltage applied and force generated, $r=0.993$, $p<0.01$
Current applied and force generated, $r=0.997$, $p<0.01$ This is achieved in practice (and in relation to FIGS. 2 & 3) by allowing the switches labelled 24 and 23 to close, while the switches 22 and 21 remain open, following each applied pulse. This provides a pathway for the charge built up on the skin to be discharged.

Through the implementation of the above step a much more forceful contraction is made possible as the user does not experience limitations in the amplitude of stimulus applied due to pain experienced at the skin surface. However, new limiting factors are introduced; muscle cramping/spasm due to the contractile force generated and a reflex response due to rapid activation of the stimulated muscle. To account for these factors and to enable greater peak muscle force generation, a new method of stimulus adjustment is required to counteract this issue.

Figure 6:
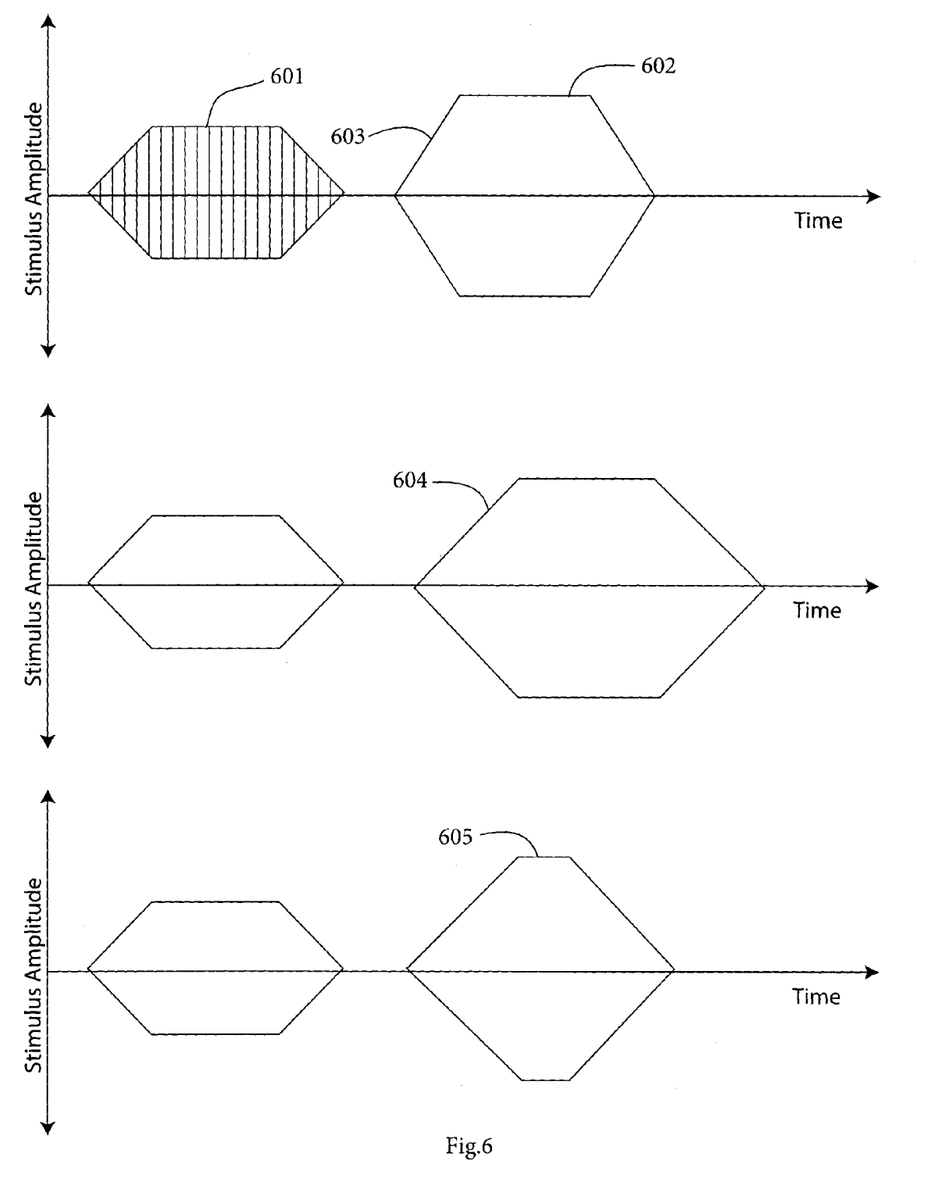
FIG. 6 shows, top panel: typical stimulus envelopes at two different intensities, and, middle/bottom, panels: alternative methods of adjusting the stimulus envelope as intensity increases.

When NMES is applied, the larger neural fibres are first to fire. To increase the contractile force, the stimulus intensity needs to be increased to recruit and fire more neural fibres. Consider the following example—At a particular low stimulus level, the first neural fibres do not fire until the envelope reaches maximum voltage (601). These neurons will stop firing when the envelope drops below this threshold. If much higher stimulus levels are applied i.e. to recruit more muscle fibres, the stimulus ramps up much faster and these same neural fibres are activated earlier (603) and remain activated for a longer period of time (604). This may lead to a greater risk of muscular pain and cramping at higher stimulus levels. Furthermore, as the ramp up rate increases the entire muscle experiences a faster rate of contraction. We have noticed that this increase in contraction rate can induce a reflex response.

To account for these limitations a number of alternative adaptive mechanisms are shown in the second and third plots of FIG. 6. Referring to the plot 604, the duration of the ramp-up period of the stimulus envelope increases with increased stimulus intensity, whilst maintaining a consistent ramp-up rate. In a second scheme illustrated by the plot 605, the on-time is reduced while the ramp-up time and ramp-down time are elongated as the stimulus intensity is increased. Again, the ramp slopes are uniform. This may be done to maintain the ramp-up rate and total envelope duration. The benefit of this case is that motor fibres supplied by the first-to-fire neural fibres will not contract for longer periods of time as the maximum stimulus intensity increases.

A similar method may be employed to increase or decrease the ramp-up rate/time, ramp-down rate/time, on-time and off-time with reference to changes in the peak stimulus intensity. This may be achieved in practice using a look-up table for each parameter. Alternatively, it may be achieved by setting the ramp-up/ramp-down rates and adjusting the on-time parameter accordingly. Alternatively, it may be achieved by setting starting conditions for each variable and a ratio determining how each parameter should be adjusted based on changes in the peak stimulus intensity.

A further advantage of this device is that a modulated voltage output may be created in real time. This mechanism is advantageous in applications such as drop-foot where a modulated stimulus intensity is required (Breen et al., 2006; Lyons & Breen, 2003). A further advantage of the stimulator device is that a programmed output waveform may be amplitude modulated by sensor control/user input. A further advantage is that the DC-DC output voltage and current available is limited. The EMCO device used (102) has been selected such that the maximum output current in the event of multiple failures (a short between the user and the DC-DC output) is 5 mA.

The high voltage is applied to the storage capacitor 103 such that the capacitor may be charged to various voltage levels. The charging of this capacitor only occurs if the switch 104 between the high voltage supply and capacitor is closed. Another advantage is that during the application of stimulus, this switch 104 may be opened, ensuring a disconnection between the high voltage power supply 102 and the user via the electrodes 110, which eliminates the requirement of an additional relay to isolate the user.

A full H-Bridge is employed such that biphasic stimulation may be applied. It is a benefit of this device that the H-Bridge is created through the use of MOSFETs. This results in faster switching, lower switching power requirements, and a simpler design requiring fewer parts. This also results in lower on-resistance (the resistance of the switch in the closed position). As the voltage delivered is split across the H-bridge and the stimulus electrodes, a reduced on-resistance reduces the voltage required for a given voltage across the stimulus electrodes. The total resistance due to the components accommodating the application of stimulus is negligible, less than 1 Ohm. A sense resister (107, 10 Ohms) provides the only significant resistance in the circuit.

For additional safety, the storage capacitor 103 can be discharged directly to ground if required by closing the switches on one side of the H-bridge. This switching configuration bypasses the electrodes/user completely.

Due to full control of the H-Bridge a test charge may be developed on the storage capacitor. This facilitates a full diagnostic procedure. Full testing of the H-bridge may be achieved at both maximum current and voltage. Our approach is to test the device integrity incrementally up to maximum voltage and to utilise the internal resistance of the device to test integrity for maximum current. Electrode impedance/reactance may then be tested by passing a voltage pulse across the electrodes.

Figure 7:
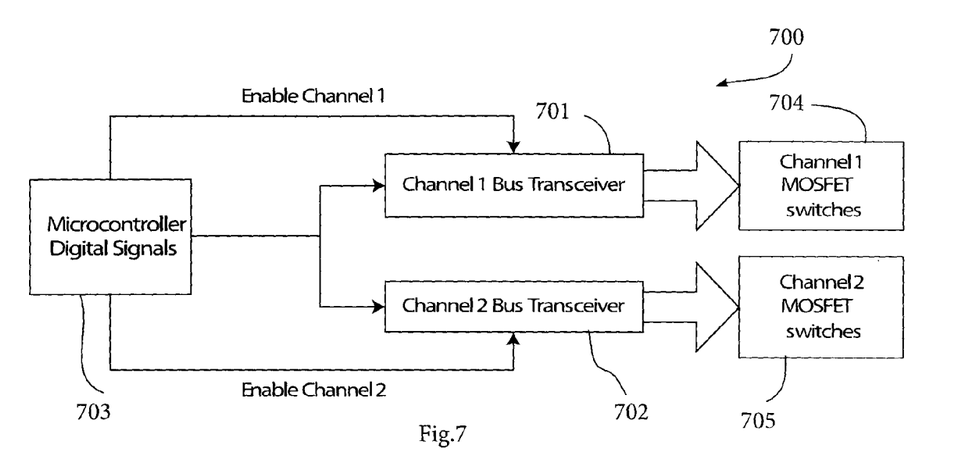
FIG. 7 is a block diagram of a device with two channels.

Referring to FIG. 7, in order to allow multiple stimulation channels of operation a selectable bus transceiver is utilised. A bus transceiver for each channel provides a safe mechanism by which each output channel may be selected at one time thereby reducing the number of control lines required. In the event of an error being detected the system can place each channel in a safe state simultaneously. The added benefit of this system is that one channel may be selectively active at a time hence automatically preventing cross stimulation. When a stimulation channel is not selected all gates in the channel are automatically opened preventing connection between the user and the HV power source. Modular extension of the stimulator is possible through the addition of additional bus-transceivers and analogue channel circuitry. This reduces the complexity of control as each channel is controlled by the same control bus but selected and enabled independently. An additional advantage is that in the event of an error being detected all channels may be disabled simultaneously. Correct functioning of the bus transceiver may be tested during start-up of the device or while the system is running. This may be achieved by polling the output of a disabled stimulus channel while an enabled stimulus channel is in operation.

Figure 8:
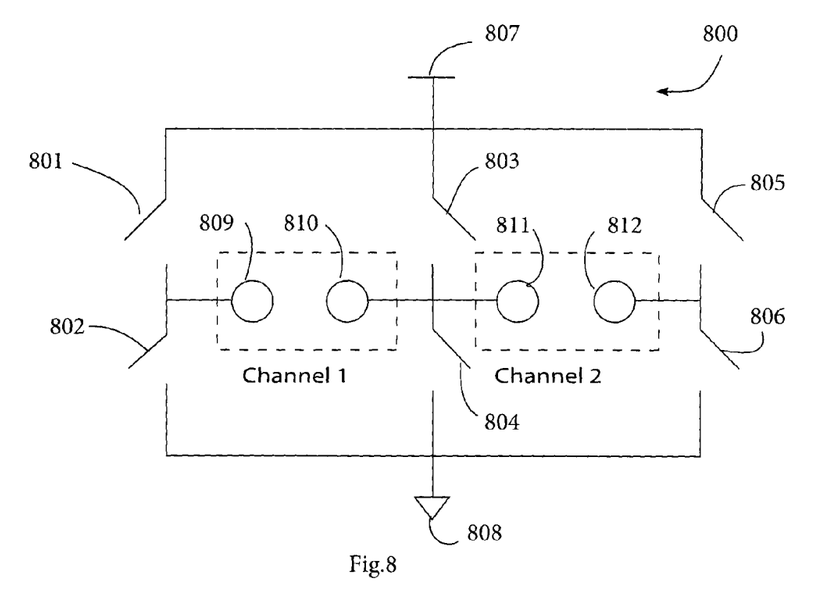
FIG. 8 is a diagram showing a series of two bridges formed by sis control switches.

Instead of using a bus transceiver, a modification can be made to the H-bridge to allow 2-channel operation through a minor circuitry addition and control features from the microcontroller. An example of the implementation is shown in FIG. 8. The two-channel implementation requires 6 switches in this modified H-bridge configuration with Channel 1 electrodes connected between nodes 809 and 810 and Channel 2 electrodes connected between nodes 811 and 812. Nodes 810 and 811 are in common. Power is delivered as before to three top switches from a charge store 807 and bottom 3 switches are connected to ground. Closing switch pairs 801 and 804 delivers a positive pulse to channel 1 and closing switch pairs 802 and 803 delivers an opposite negative pulse to channel 1. To deliver a pulse to channel 2, one must close switch pairs 805 and 804 for a positive pulse or close switch pairs 803 and 806 for an opposite negative pulse. Delivering a pulse to the electrodes of Channel 2 will not result in a pulse being delivered to the electrodes of channel 1 as the circuit of channel 1 is not completed.

This configuration allows for both sequential stimulation of muscles (e.g. full contraction cycle of muscle A followed by full contraction cycle of muscle B) as well as the simultaneous stimulation of muscles. Simultaneous stimulation of muscles is achieved by interleaving pulses between the gaps in the pulse-train.

Figure 9:
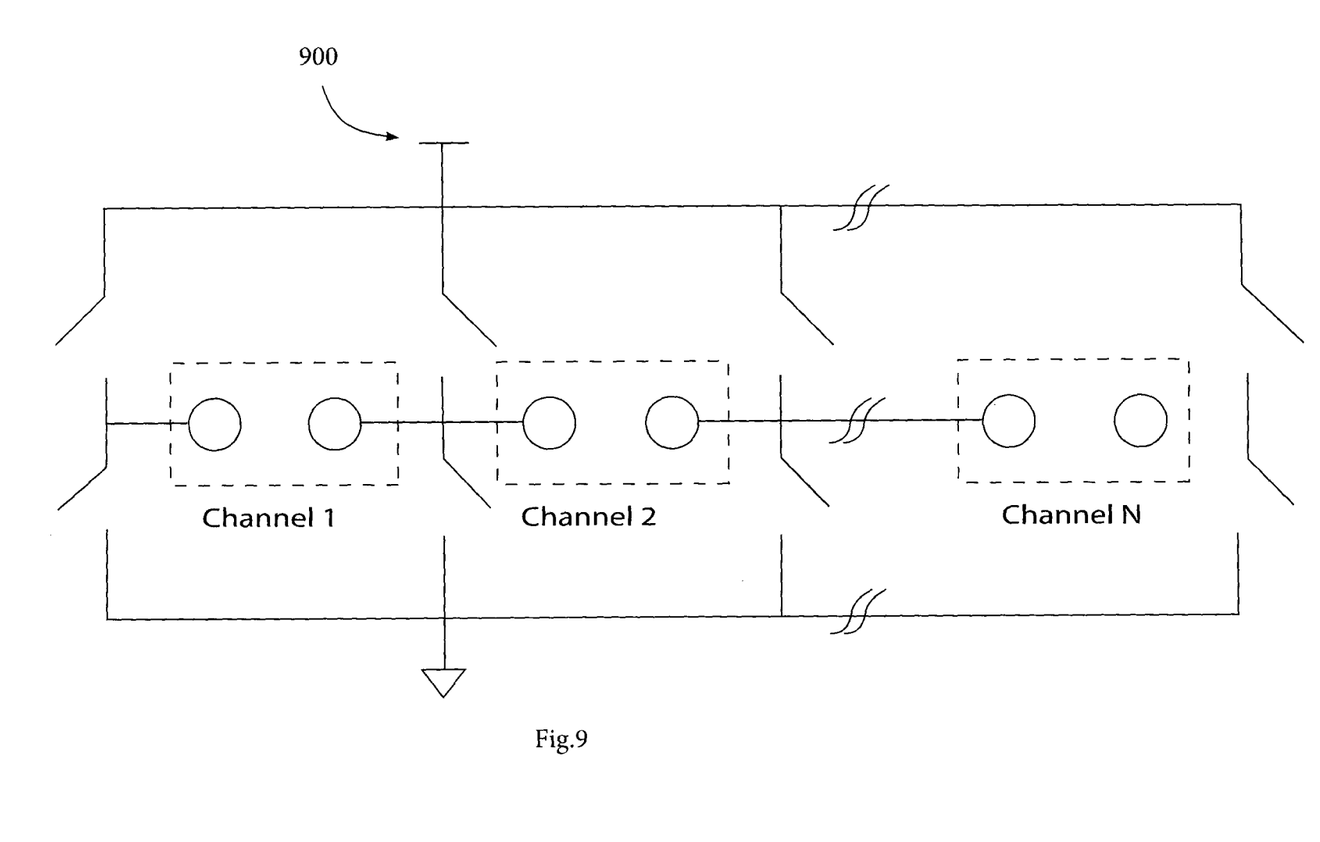
FIG. 9 is a generalised diagram for providing N channels with only one high voltage supply and one isolation capacitor.

Those skilled in the art will realise that the aforementioned configuration can be extended further to include multiple channels of stimulation by adding further pairs of switches to the H-bridge as shown by a bridge arrangement 900 in FIG. 9. The number of channels is restricted only by the desired pulse width and frequency of stimulation. Another advantage is that the device can create stimulus output pulse trains in any required modulation. Examples include monophasic, biphasic, biphasic with alternating initial pulse, frequency modulated, amplitude modulated and combinations of these.

The invention is not limited to the embodiments described but may be varied in construction and detail.

The invention claimed is:

1. A surface neuromuscular electrical stimulation device comprising:
    a voltage regulator connected to a high voltage supply,
    a bridge of control switches including top switches and bottom switches,
    a control processor configured to direct drive signals for the bridge of control switches,
    electrode terminals connected in the bridge to receive the drive signals via the control switches,
    a ground connected to the electrode terminals, and
    at least one isolation capacitor configured to isolate the high voltage supply from the electrode terminals,
    wherein the control processor is configured to direct the drive signals for the bridge of control switches in which charge build-up on the electrode terminals is allowed to dissipate to the ground in an inter-pulse interval, and
    wherein the top switches are linked with the at least one isolation capacitor and the bottom switches are linked to the ground.

2. The stimulation device as claimed in claim 1, wherein the device includes a voltage sensor for sensing voltage in the high voltage supply, and the control processor is adapted to monitor said voltage and to determine further stimulation control accordingly.

3. The stimulation device as claimed in claim 1, wherein the device includes a current sensor for sensing current in the bridge, and the control processor is adapted to monitor said current and to determine further stimulation control accordingly.

4. The stimulation device as claimed in claim 1, wherein the device includes a current sensor for sensing current in the bridge, and the control processor is adapted to monitor said current and to determine further stimulation control accordingly; and wherein the control processor is adapted to use said current sensing to monitor changes in at least one of skin impedance and reactance in real time.

5. The stimulation device as claimed in claim 1, wherein the device includes a current sensor for sensing current in the bridge, and the control processor is adapted to monitor said current and to determine further stimulation control accordingly; and wherein the control processor is adapted to use said current sensing to monitor changes in at least one of skin impedance and reactance in real time; and wherein the current sensor includes a feedback conductor arranged to provide feedback of a sensing signal from a resistance connected to the bottom bridge control switches.

6. The stimulation device as claimed in claim 1, wherein the device includes a current sensor for sensing current in the bridge, and the control processor is adapted to monitor said current and to determine further stimulation control accordingly; and wherein the control processor is adapted to use said current sensing to monitor changes in at least one of skin impedance and reactance in real time; and wherein the current sensor includes a feedback conductor arranged to provide feedback of a sensing signal from a resistance connected to the bottom bridge control switches; and wherein the current sensor further includes a current-limiting resistor connected to the bottom bridge control switches and a Zener diode in series with the resistor to protect the feedback conductor from over-current and over-voltage.

7. The stimulation device as claimed in claim 1, wherein the device includes a current sensor for sensing current in the bridge, and the control processor is adapted to monitor said current and to determine further stimulation control accordingly; and wherein the control processor is adapted to use a combination of said current sensing in the bridge and said voltage sensing in the high voltage supply to ensure that only a voltage required across the electrodes is applied and that the stimulation ceases if any fault is detected.

8. The stimulation device as claimed in claim 1, wherein the control switches includes at least four switches in a H-bridge arrangement in which the electrode terminals are connected across the middle of the bridge, power is delivered to the top switches from the capacitor and the bottom switches are connected to ground, wherein closing a top and a bottom switch of the bridge allows the stored charge to flow through the electrodes to ground, generating a positive pulse, and closing the other two switches allows the charge to flow in the opposite direction and generates a relative negative pulse.

9. The stimulation device as claimed in claim 1, wherein the control processor is adapted to provide the drive signals including:
    applying a current pulse causing a build-up of charge concentrated at the electrode terminals,
    applying a second pulse of opposite polarity,
    in the interval between said pulses causing the electrode terminals charge to dissipate to ground by closing the bottom bridge switches, thereby reducing the peak current of the second pulse.

10. The stimulation device as claimed in claim 1, wherein the control processor is adapted to close the bottom bridge control switches to allow charge built-up within the electrode terminals to flow through the electrodes to ground.

11. The stimulation device as claimed in claim 1, wherein the control processor is adapted to vary ramp times for voltage increases and decreases of the high voltage supply according to conditions while maintaining a constant ramp slope.

12. The stimulation device as claimed in claim 1, wherein the control processor is adapted to vary ramp times for voltage increases and decreases of the high voltage supply according to conditions while maintaining a constant ramp slope; and wherein at least one of the ramp-up and ramp-down time of the stimulus envelope increases with increased stimulus intensity.

13. The stimulation device as claimed in claim 1, wherein the control processor is adapted to vary ramp times for voltage increases and decreases of the high voltage supply according to conditions while maintaining a constant ramp slope; and wherein the on-time is reduced while the ramp-up time and ramp-down time are elongated as the stimulus intensity is increased, to maintain the ramp-up rate and total envelope duration.

14. The stimulation device as claimed in claim 1, wherein the control processor is adapted to change ramp rates in response to changes in the peak stimulus intensity.

15. The stimulation device as claimed in claim 1, wherein the control processor is adapted to change ramp rates in response to changes in the peak stimulus intensity; wherein the control processor is adapted to make said changes by reference to a look-up table for parameters or by setting the ramp-up/ramp-down rates and adjusting the on-time parameter accordingly, or by setting starting conditions for each variable and a ratio determining how each parameter should be adjusted based on changes in the peak stimulus intensity.

16. The stimulation device as claimed in claim 1, wherein the isolation capacitor value is no higher than 10 µF, thereby limiting the DC-DC output voltage and current delivered to the bridge.

17. The stimulation device as claimed in claim 1, wherein the isolation capacitor value is no higher than 10 µF, thereby limiting the DC-DC output voltage and current delivered to the bridge; wherein the maximum output current in the event of multiple failures (a short between the user and the DC-DC output) is 5 mA.

18. The stimulation device as claimed in claim 1, wherein the total resistance due to the bridge control switches which are ON at any time for delivery of power to the electrodes is less than 10 Ohms.

19. The stimulation device as claimed in claim 1, wherein the device includes a switch arranged to dump charge from the isolation capacitor to ground bypassing the bridge in the event of a failure detected by the control processor.

20. The stimulation device as claimed in claim 1, wherein the device includes a plurality of stimulation channels.

21. The stimulation device as claimed in claim 1, wherein the device includes a plurality of stimulation channels; and wherein the device includes at least six switches, in which each successive pair of top and bottom switches forms a bridge with the preceding pair of top and bottom switches.

22. The stimulation device as claimed in claim 1, wherein the device includes a plurality of stimulation channels; and wherein the device includes at least six switches, in which each successive pair of top and bottom switches forms a bridge with the preceding pair of top and bottom switches; and wherein the device includes only one high voltage supply and one isolation capacitor feeding the control switches forming the bridges.

23. The stimulation device as claimed in claim 1, wherein the control processor is adapted to apply a test charge to the isolation capacitor and to then perform a full diagnostic procedure with both maximum current and voltage applied.

24. The stimulation device as claimed in claim 1, wherein the control processor is adapted to apply a test charge to the isolation capacitor and to then perform a full diagnostic procedure with both maximum current and voltage applied; and wherein said testing includes incrementally increasing voltage across the isolation capacitor up to a maximum voltage and utilizing the internal resistance of the device to test integrity for maximum current, and then testing electrode impedance and reactance by passing a voltage pulse across the electrodes.

25. A surface neuromuscular electrical stimulation device comprising:
a voltage regulator connected to a high voltage supply,
a bridge of control switches including top switches and bottom switches,
a control processor configured to direct drive signals for the bridge of control switches,
electrode terminals connected in the bridge to receive the drive signals via the control switches,
a ground connected to the electrode terminals, and
at least one isolation capacitor configured to isolate the high voltage supply from the electrode terminals,
wherein the control processor is configured to direct the drive signals for the bridge of control switches in which charge build-up on the electrode terminals is allowed to dissipate to the ground in an inter-pulse interval,
wherein the top switches are linked with the at least one isolation capacitor and the bottom switches are linked to the ground, and
wherein the control processor is configured to apply a test charge to the isolation capacitor and to then perform a full diagnostic procedure with both maximum current and voltage applied.

26. A surface neuromuscular electrical stimulation device comprising:
a voltage regulator connected to a high voltage supply,
a bridge of control switches including top switches and bottom switches,
a control processor configured to direct drive signals for the bridge of control switches,
electrode terminals connected in the bridge to receive the drive signals via the control switches,
a ground connected to the electrode terminals, and
at least one isolation capacitor configure to isolate the high voltage supply from the electrode terminals,
wherein the processor is configured to direct the drive signals for the bridge of control switches in which charge build-up on the electrode terminals is allowed to dissipate to the ground in an inter-pulse interval,
wherein the top switches are linked with the at least one isolation capacitor and the bottom switches are linked to the ground,
wherein the control processor is configured to apply a test charge to the isolation capacitor and to then perform a full diagnostic procedure with both maximum current and voltage applied; and
wherein said testing includes incrementally increasing voltage across the isolation capacitor up to a maximum voltage and utilizing the internal resistance of the device to test integrity for maximum current, and then testing electrode impedance and reactance by passing a voltage pulse across the electrodes.

* * * * *